United States Patent
Kinsho et al.

(10) Patent No.: US 9,499,468 B2
(45) Date of Patent: Nov. 22, 2016

(54) 3-ACYLOXYMETHYL-3-BUTENYL CARBOXYLATE COMPOUND AND METHOD FOR PRODUCING 4-ALKYL-3-METHYLENEBUTYL CARBOXYLATE

(71) Applicant: Shin-Etsu Chemical Co., Ltd., Tokyo (JP)

(72) Inventors: Takeshi Kinsho, Joetsu (JP); Naoki Ishibashi, Joetsu (JP); Yusuke Nagae, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 14/974,104

(22) Filed: Dec. 18, 2015

(65) Prior Publication Data
US 2016/0185707 A1 Jun. 30, 2016

(30) Foreign Application Priority Data
Dec. 25, 2014 (JP) ................. 2014-262614

(51) Int. Cl.
| | | |
|---|---|---|
| C07C 67/297 | (2006.01) | |
| C07C 67/293 | (2006.01) | |
| C07C 67/11 | (2006.01) | |
| C07C 69/003 | (2006.01) | |
| C07C 69/02 | (2006.01) | |
| C07C 69/28 | (2006.01) | |
| C07C 69/34 | (2006.01) | |

(52) U.S. Cl.
CPC ............ *C07C 67/297* (2013.01); *C07C 67/11* (2013.01); *C07C 67/293* (2013.01); *C07C 69/003* (2013.01); *C07C 69/02* (2013.01); *C07C 69/28* (2013.01); *C07C 69/34* (2013.01)

(58) Field of Classification Search
CPC ... C07C 17/358; C07C 21/14; C07C 67/293; C07C 67/145
See application file for complete search history.

(56) References Cited

U.S. PATENT DOCUMENTS

| | | |
|---|---|---|
| 3,388,192 A | 6/1968 | Machleidt et al. |
| 4,745,229 A | 5/1988 | Otera et al. |

FOREIGN PATENT DOCUMENTS

GB 2111501 A 7/1983

OTHER PUBLICATIONS

Zaragoza Dorwald, Side Reactions in Organic Synthesis, 2005, Wiley-VCH Verlag GmbH & Co. KGaA, Weinheim, Preface. p. IX.*
Ochiai et al, Chemical & Pharmaceutical Bulletin, Iodine(III)-Mediated Allylation of Aromatic Compounds and Alcohols Using Allylmetal (Group IVb) Compounds, 1985, 33(1), pp. 41-47.*
Gieselmann et al. "Sex Pheromone of the San Jose Scale", *J. Chem. Ecol.* 5(6):891-900 (1979).
Anderson et al. "Synthesis of 7-Methyl-3-Methylene-7-Octen-1-YL Propanoate and (Z)-3,7-Dimethyl-2,7-Octadien-1-YL Propanoate, Components of the Sex Pheromone of the San Jose Scale", *J. Chem. Ecol.* 5(6):919-927 (1979).
Weiler et al. "The synthesis of the isomeric componenets of San Jose scale pheromone—and illustration of a stereospecific synthesis of trisubstituted alkenes", *Can. J. Chem.* 71:1955-1963 (1993).
Weedon et al. "Photoenolisation of Conjugated Esters: Synthesis of a San Jose Scale Pheromone by Partially Regio-Controlled Photochemical Deconjugation", *Tetrahedron Letters* 27(46):5555-5558 (1986).
Zhang et al. "Modification of Wolinsky's Ene-Chlorination", *Chinese Chemical Letters* 2(8):611-612 (1991).
Huaxue Tongbao pp. 40-42 (1994).

(Continued)

*Primary Examiner* — Paul A Zucker
(74) *Attorney, Agent, or Firm* — Myers Bigel, P.A.

(57) ABSTRACT

Provided is a simple, selective and efficient method for producing 4-alkyl-3-methylenebutyl carboxylates such as 7-methyl-3-methylene-7-octenyl propionate. More specifically provided is a method for producing a 4-alkyl-3-methylenebutyl carboxylate compound, the method comprising a diacyloxylation step of subjecting a 4-halo-2-halomethyl-1-butene compound (6) to diacyloxylation to obtain a 3-acyloxymethyl-3-butenyl carboxylate compound (3), and a coupling step of subjecting the 3-acyloxymethyl-3-butenyl carboxylate compound (3) to a coupling reaction with an organometallic reagent (4) to obtain the 4-alkyl-3-methylenebutyl carboxylate compound (5).

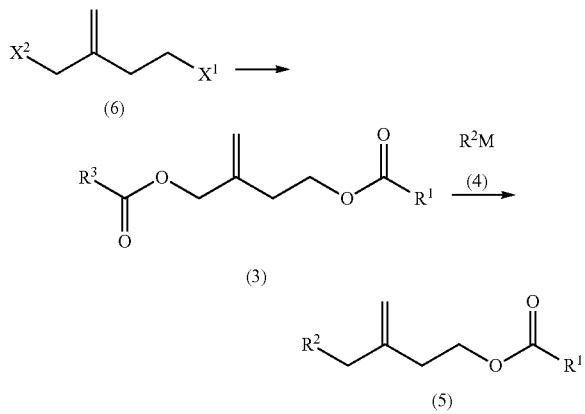

6 Claims, 1 Drawing Sheet

(56) References Cited

OTHER PUBLICATIONS

Chong et al. "Studies on the Alkylation of 3-Methyl-3-buten-1-ol Dianion: An Efficient Synthesis of 3-Methylene-1-alkanols Including a San Jose Scale Sex Pheromone", *J. Org. Chem*, 66:8248-8251 (2001).

Veselovskii et al "Synthesis of α-Myrcenol Acetate and Propionate from Isobutenylcarbinol", *Izvestiya Akademii Nauk SSSR, Seriya Khimicheskaya* 3:513-516 (1990).

Aldrich et al. "Identification of Presumed Pheromone Blend from Australasian Predaceous Bug, *Oechalia schellengergii* (Heteroptera: Pentatomidae)", *J. Chem. Ecol.* 22(4):729-738 (1996).

Kozyrkov et al. "A Simple and Efficient Conversion of Tertiary Cyclopropanols to 2-Substituted Allyl Halides", *Synlett* 3:443-446 (2002).

Kulinkovich et al. "A Convenient Way for the Conversion of Carboxylic Esters into 2-Substituted Allyl Halides", *Synthesis* 10:1713-1717 (2005).

European Search Report corresponding to European Application No. 15200348 dated Apr. 21, 2016.

Bailey et al. "Pyrolysis of Esters. XXI. 2-Hydroxymethyl-1,2-butadiene", *J. Org. Chem*. pp. 1975-1978 (1962).

Ferraboschi et al. "Regio- and Enantioselectivity of *Pseudomonas cepacia* Lipase in the Transesterification of 2-Substituted-1,4-Butanediols", *Tetrahedron Asymmetry* 5(4):691-698 (1994).

Li et al. "Approaches to selective isoprenologation via reactions of ($\eta^3$-ally)Fe(CO)$^+$4 with allyl nucleophiles", *J. Organometallic Chem*. 402:105-112 (1991).

Tabuchi et al. "Total Synthesis of Alternaric Acid", *Tetrahedron Letters* 34(14):2327-2330 (1993).

Wade et al. "Thermolytic Rearrangements of 1,1-Cyclopropanedimethanol Disulfonates: Cyclopropylcarbinyl Cations Revisted", *J. Org. Chem*. 58:3140-3147 (1993).

European Search Report corresponding to European Application No. 15200346 dated Apr. 20, 2016.

\* cited by examiner

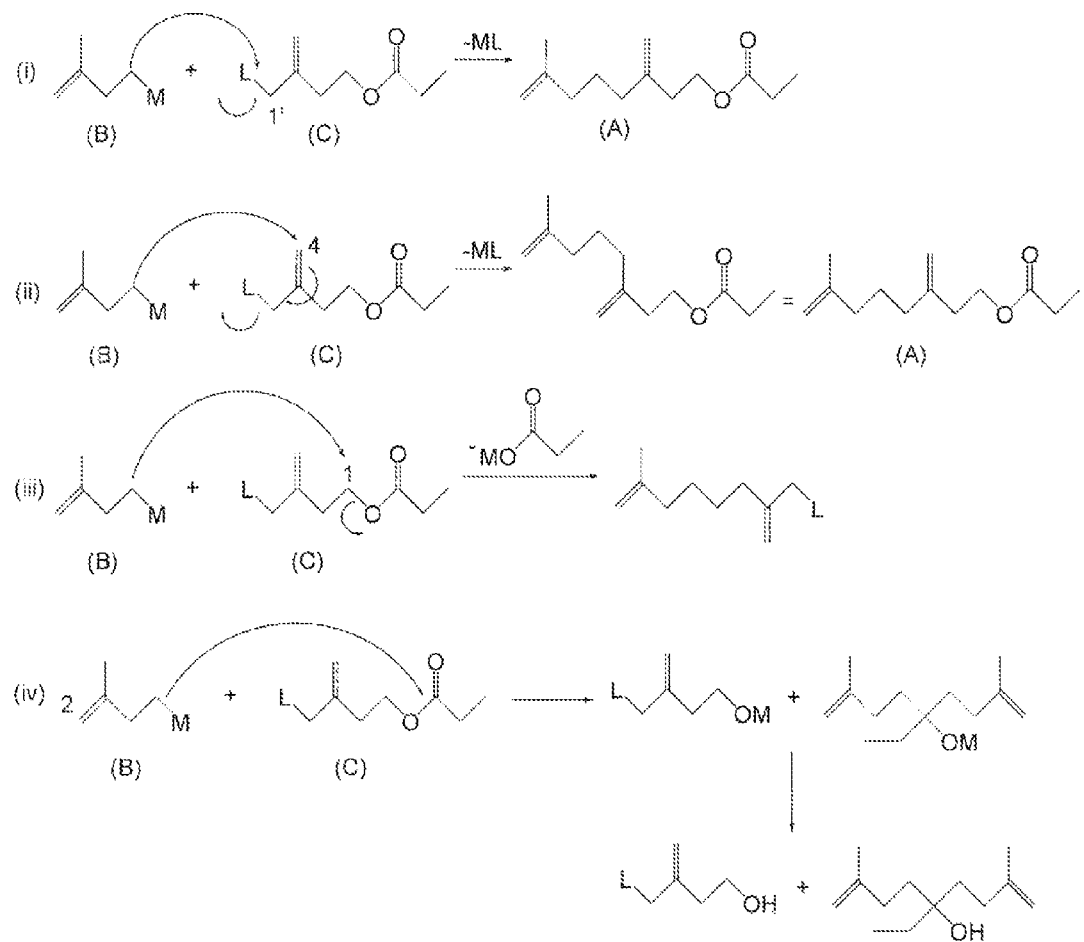

3-ACYLOXYMETHYL-3-BUTENYL CARBOXYLATE COMPOUND AND METHOD FOR PRODUCING 4-ALKYL-3-METHYLENEBUTYL CARBOXYLATE

RELATED APPLICATION

This application claims priority from Japanese Patent Application No. 2014-262614, filed Dec. 25, 2014, the disclosure of which is incorporated by reference herein in its entirety.

FIELD AND BACKGROUND OF THE INVENTION

The present invention relates to a method for producing a 4-alkyl-3-methylenebutyl carboxylate that is useful as a bioactive substance such as an insect pheromone and a substance relating thereto and as a synthetic intermediate in organic synthetic chemistry. For example, the present invention relates to a method for producing 7-methyl-3-methylene-7-octenyl propionate, which is, for example, a major component of the sex pheromone of *Quadraspidiotus perniciosus* (Comstock) (generic name: San Jose Scale).

The sex pheromones of insects are biologically active substances that are commonly secreted by female individuals and have the function of attracting male individuals. A small amount of the sex pheromone shows strong attractive activities. The sex pheromone has been widely used as means for forecasting insect emergence or for ascertaining regional spread (invasion into a specific area) and as means for controlling an insect pest. As the means for controlling insect pests, control methods called mass trapping, lure and kill (another name: attract and kill), lure and infect (another name: attract and infect), and mating disruption are widely used in practice. To utilize the sex pheromone, economical production of a required amount of the pheromone product is demanded for basic research and also for application.

*Quadraspidiotus perniciosus* (generic name: San Jose Scale, hereinafter abbreviated as "SJS") is widely distributed in the world, damages fruit trees and ornamental trees, especially deciduous fruit trees, and thus is an economically critical insect pest. As for the sex pheromone of SJS, three compounds of 7-methyl-3-methylene-7-octenyl propionate, (Z)-3,7-dimethyl-2,7-octadienyl propionate, and (E)-3,7-dimethyl-2,7-octadienyl propionate have been identified as the active components by Gieselmann et al. (J. Chem. Ecol., 5, 891 (1979)).

These sex pheromone compounds of SJS are isomers to each other, and there is a demand for a selective production method of each compound for basic biological studies and agronomic studies. There is also a strong demand for an efficient production method capable of supplying a sufficient amount of the pheromone product for the purposes of application and practical use.

Examples of the synthesis of 7-methyl-3-methylene-7-octenyl propionate, which is the major component of the sex pheromone of SJS, include the following Syntheses (a) to (f):

Synthesis (a) comprising addition of an organocuprate reagent to alkyne as a key reaction, by Anderson et al. (J. Chem. Ecol., 5, 919 (1979));

Synthesis (b) comprising a one-carbon homologation step of a β-keto ester compound, 7-methyl-3-oxo-7-octenoate, by Weiler et al. (Can. J. Chem., 71, 1955 (1993));

Synthesis (c) comprising photochemical position isomerization of a double bond of an α,β-unsaturated ester to a β,γ-unsaturated ester as a key reaction, by Weeden et al. (Tet. Lett., 27, 5555 (1986));

Synthesis (d) comprising exo-methylene formation as a key reaction by reduction of allylic chloride obtained by chlorination involving isomerization of a trisubstituted double bond, by Zhang et al. (Chinese Chemical Letters, 2, 611 (1991), Huaxue Tongbao, 40, (1994));

Synthesis (e) by alkylation of a dianion of 3-methyl-3-buten-1-ol, by Anderson et al. (J. Chem. Ecol., 5, 919 (1979)) and Chong et al. (J. Org. Chem., 66, 8248 (2001)); and Synthesis (f) which is a nonselective synthesis through an allylic chloride mixture, by Veselovskii et al. (Izvestiya Akademii Nauk SSSR, Seriya Khimicheskaya, 3, 513 (1990)).

SUMMARY OF THE INVENTION

These synthetic methods unfortunately involve a lot of difficulties in order to selectively synthesize 7-methyl-3-methylene-7-octenyl propionate in a high yield on an industrial scale. For example, the difficulties arise from the use of reagents that are expensive or difficult to handle on an industrial scale, including an organolithium reagent such as n-butyllithium and methyllithium in Syntheses (b) and (e), lithium aluminum hydride (LAH) in Syntheses (a), (b) and (d), a stoichiometric amount of an organocuprate reagent in Synthesis (a), a Tebbe reagent in Synthesis (b), and sulfuryl chloride in Synthesis (f). In the synthetic route in which a double bond is intentionally isomerized even by the photochemical isomerization in Synthesis (c) or the isomerization through allylic chloride in Synthesis (d), undesired isomers are unfortunately formed in small amounts as by-products and thus are required to be removed even if the isomerization is achieved with a comparatively high selectivity. The synthesis in Synthesis (f), in which unintended isomers are mixed with a synthetic intermediate, also has significant problems because a target compound is difficult to separate from isomers thereof and the yield is lowered. In Syntheses (a) to (f), intermediates and a target compound are isolated or purified by various types of chromatography, which are difficult to perform on an industrial scale. As described above, the existing syntheses are considered to be very difficult to economically obtain a sufficient amount of the product on an industrial scale.

In view of the above circumstances, an object of the present invention is to provide a simple, selective and efficient production method in order to supply a sufficient amount of 4-alkyl-3-methylenebutyl carboxylate such as 7-methyl-3-methylene-7-octenyl propionate, which is a major component of the sex pheromone of SJS and is required for biological studies, agronomic studies, actual application and utilization, and the like.

As a result of intensive studies, the inventors of the present invention have found that by selecting reagents and conditions that can be easily achieved on an industrial scale, a 4-alkyl-3-methylenebutyl carboxylate compound can be synthesized with a high selectivity, and have completed the present invention.

In an aspect of the present invention, there is provided a method for producing a 4-alkyl-3-methylenebutyl carboxylate compound, the method comprising: a diacyloxylation step of subjecting a 4-halo-2-halomethyl-1-butene compound represented by General Formula (6) to diacyloxylation to obtain a 3-acyloxymethyl-3-butenyl carboxylate compound represented by General Formula (3), and a coupling step of subjecting the 3-acyloxymethyl-3-butenyl carboxylate compound (3) to a coupling reaction with an organometallic reagent represented by General Formula (4) to obtain the 4-alkyl-3-methylenebutyl carboxylate compound represented by Formula (5).

In General Formulae, $X^1$ and $X^2$ may be the same or different and each represents a halogen atom; $R^1$, $R^2$ and $R^3$ may be the same or different and each represents a monovalent hydrocarbon group having 1 to 10 carbon atoms and optionally containing one or more unsaturated bonds; and M represents a cationic moiety.

In another aspect of the present invention, there is provided a 4-acyloxy-3-methylenebutyl carboxylate compound represented by General Formula (3).

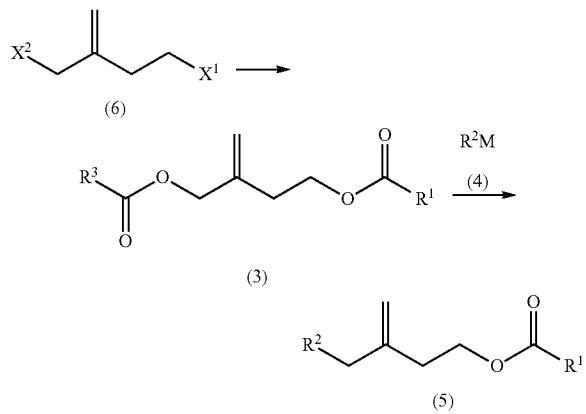

According to the present invention, a 4-alkyl-3-methylenebutyl carboxylate compound such as 7-methyl-3-methylene-7-octenyl propionate can be selectively and efficiently synthesized through a useful intermediate, 3-acyloxymethyl-3-butenyl carboxylate compound.

BRIEF DESCRIPTION OF THE DRAWINGS

FIG. 1 is a reaction scheme in the synthesis of a 4-alkyl-3-methylenebutyl carboxylate compound.

DETAILED DESCRIPTION OF THE PREFERRED EMBODIMENTS

The present invention now will be described more fully hereinafter in which embodiments of the invention are provided with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. Unless otherwise defined, all technical and scientific terms used herein have the same meaning as commonly understood by one of ordinary skill in the art to which this invention belongs. All references cited are incorporated herein by reference in their entirety.

The chemical formulae of intermediates, reagents, and target compounds in the present specification can include isomers that differ in substitution sites and stereoisomers such as enantiomers and diastereomers in terms of structure. Unless otherwise stated, each chemical formula is intended to represent all the isomers in each case. These isomers may be used singly or as a mixture.

The inventors of the present invention have considered the synthetic route of 4-alkyl-3-methylenebutyl carboxylate compounds as follows: One of the target 4-alkyl-3-methylenebutyl carboxylate compounds, 7-methyl-3-methylene-7-octenyl propionate (A), which is a major component of the sex pheromone of SJS, will be described as an example. In order to build the carbon framework having 10 carbon atoms of the target compound (A) in consideration of easy availability and cost efficiency of raw materials, if two building blocks each having 5 carbon atoms in the below formula can be used to form a bond, in other words, if an organometallic reagent (B) as a nucleophile and an electrophile (C) having 5 carbon atoms and having a leaving group L and a propionyloxy group, which is a functional group present on the target compound, can undergo a coupling reaction in such a manner that the leaving group L is eliminated, it is considered that a straightforward and efficient synthesis can be achieved through a short process.

It is considered that the electrophile (C) can be prepared from a known 1-(2-haloethyl)cyclopropanol compound (D) by performing the following reactions that are combined in an appropriate order: (1) sulfonylation of the hydroxy group; (2) a halogenation reaction involving cyclopropyl-allyl rearrangement of the obtained cyclopropyl sulfonate; and (3) a propionyloxylation reaction of the halogen group X into propionate.

In the following reaction equation, the hollow arrows represent transformation in a retrosynthetic analysis, L represents a leaving group, and M represents a cationic moiety. The small numeric characters attached on the compound (C) represent the position numbers of carbons.

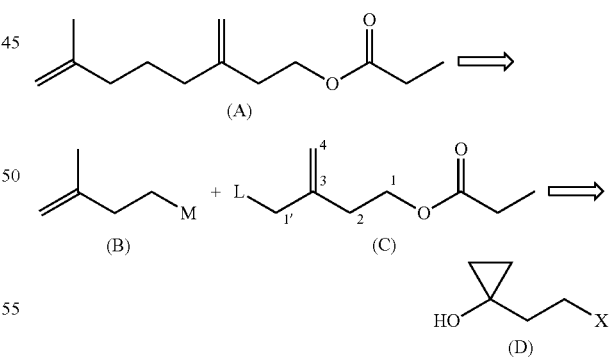

In the retrosynthetic analysis, it is important to achieve the selectivity of the coupling reaction between the nucleophile (B) and the electrophile (C). The reaction sites in the electrophile (C) capable of forming a carbon-carbon bond with the nucleophile (B) can be the carbons at the 1-position, the 1'-position, and the 4-position. FIG. 1 presents the reaction scheme (i) in which the carbon at the 1'-position of the electrophile (C) undergoes the coupling reaction, the reaction scheme (ii) in which the carbon at the 4-position undergoes the coupling reaction, the reaction scheme (iii) in which the carbon at the I-position undergoes the coupling reaction, and the reaction scheme (iv) in which an addition reaction occurs at the carbonyl group of the propionyloxy group.

In the reaction scheme (i), a nucleophilic attack occurs at the carbon at the 1'-position to lead to the $S_N2$ reaction (bimolecular nucleophilic substitution reaction), and L is eliminated to obtain the target compound (A). In the reaction scheme (ii), a nucleophilic attack occurs at the carbon at the 4-position to lead to a substitution reaction involving allylic rearrangement that is called an $S_N2'$ reaction. Also in this scheme, L is expected to be eliminated to obtain the same target compound (A).

On the other hand, in the reaction scheme (iii), it is supposed that a nucleophilic attack occurs at the carbon at the 1-position and the propionyloxy group is eliminated to give a product that differs from the target compound (A). In the reaction scheme (iv), it is supposed that the addition reaction proceeds at the carbonyl group of the propionyloxy group to give a product that differs from the target compound (A). In addition, when the leaving group L is an acyloxy group, the carbonyl group of the acyloxy group provides a product that differs from the target compound (A).

From the above consideration, the selectivity of advancing the coupling reaction in which a nucleophilic attack occurs at the carbon at the 1'-position or the carbon at the 4-position of the electrophile (C) to eliminate the leaving group L prior to the coupling reaction at the 1-position and prior to the addition reaction to a carbonyl group is preferably achieved for the purpose. In the synthetic strategy, the leaving group L at the 1'-position and the propionyloxy group at the 1-position in the compound (C) differ in the substitution positional relation with regard to the double bond. In other words, the leaving group L is at an allylic position, while the propionyloxy group is at a homoallylic position. It is thus considered that the intended selectivity can be achieved by selecting the type of the leaving group L and reaction conditions.

As a result of repeated studies based on the above consideration, an efficient synthesis having an intended high selectivity has been achieved. Embodiments of the present invention will now be described in detail. It should not be construed that the present invention is limited to or by them.

According to the invention, a 4-halo-2-halomethyl-1-butene compound (6) as the starting material can be obtained as shown in the following reaction equation in which a 1-(2-haloethyl)cyclopropanol is subjected to sulfonylation to obtain a 1-(2-haloethyl)cyclopropyl sulfonate compound (1), and then the compound (1) is subjected to halogenation involving cyclopropyl-allyl rearrangement, in accordance with the document (Kulinkovich et. al., Synthesis, 2005, 1713).

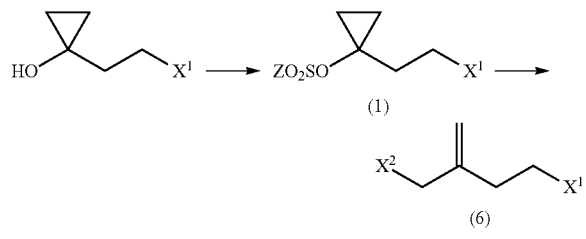

$X^1$ and $X^2$ may be the same or different and each represents a halogen atom. Each of $X^1$ and $X^2$ is preferably a chlorine atom, a bromine atom or an iodine atom.

Z represents a hydrocarbon group having 1 to 10 carbon atoms and optionally containing one or more unsaturated bonds, and is preferably an alkyl group having 1 to 10 carbon atoms or an aryl group having 6 to 10 carbon atoms, the alkyl and aryl groups optionally containing one or more unsaturated bonds. The alkyl group having 1 to 10 carbon atoms is a chain, branched, or cyclic monovalent hydrocarbon group and examples thereof preferably include a linear saturated alkyl group such as a methyl group, an ethyl group, an n-propyl group and an n-butyl group. Examples of the aryl group having 6 to 10 carbon atoms include a phenyl group, a tolyl group, a xylyl group and a naphthyl group. Specifically preferred examples of Z include a methyl group, an n-butyl group, a phenyl group and a p-tolyl group.

Next, the diacyloxylation reaction step of subjecting the 4-halo-2-halomethyl-1-butene compound (6) to diacyloxylation into a 3-acyloxymethyl-3-butenyl carboxylate compound (3) will be described.

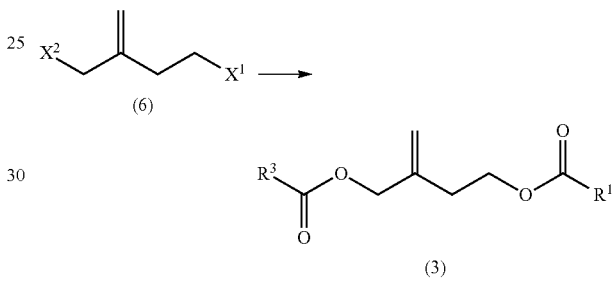

$R^1$ may be selected to be a group corresponding to the structure of a final target compound of the synthesis. $R^1$ and $R^3$ may be the same or different and are preferably the same from the viewpoint of preventing the reaction system or the products from becoming complicated.

$R^1$ and $R^3$ may be the same or different and each represents a chain, branched or cyclic monovalent hydrocarbon group having 1 to 10 carbon atoms and optionally containing one or more unsaturated bonds. $R^1$ may be selected to be a group corresponding to the structure of a final target compound of the synthesis. Examples of $R^1$ include a linear monovalent hydrocarbon group such as a methyl group, an ethyl group, an n-propyl group, an n-butyl group, an n-pentyl group, an n-hexyl group, an n-heptyl group, an n-octyl group, an n-nonyl group, an n-decyl group, a vinyl group, a 1-propenyl group, an allyl group, a 1-butenyl group, a 2-butenyl group, a 3-butenyl group, a 1-pentenyl group, a 2-pentenyl group, a 5-hexenyl group, a 1-heptenyl group, a 9-decenyl group, a 1,3-butadienyl group, a 1,3-pentadienyl group, a 1,5-hexadienyl group and an ethynyl group; a branched monovalent hydrocarbon group such as an isopropyl group, a 2-ethylpropyl group, a t-butyl group, a sec-butyl group, an isobutyl group, a t-amyl group, a neopentyl group, a 1-methylbutyl group, a 1-propylbutyl group, a 2-methylbutyl group, a 3-methylbutyl group, a 1-methylpentyl group, a 1-ethylpentyl group, an isopropenyl group, a 1-methyl-1-propenyl group, a 2-methyl-1-propenyl group, a 1-methyl-1-butenyl group, a 1,1-dimethyl-3-butenyl group, a 1-ethyl-1-pentenyl group, a 2,6-dimethyl-5-heptenyl group, a 2,6-dimethyl-1,5-heptadienyl group, a 2,6-dimethyl-1,6-heptadienyl group, a 6-methyl-2-methylene-5-heptenyl group, a 6-methyl-2-methylene-6-heptenyl group, a 4-methyl-1-pentenyl-3-pentenyl group and a 1-isopropylidene-4-methyl-3-pentenyl group; and a cyclic monovalent hydrocarbon group such as a cyclopropyl group, a 2-methylcyclopropyl group, a 2,2,3,3-tetramethylcyclopropyl group, a cyclobutyl group, a cyclopentyl group, a cyclopentylmethyl group, a 2-cyclopentylethyl group, a cyclohexyl group, a cyclohexylmethyl group, a dicyclohexylmethyl group, a 2-cyclohexylethyl group, a 3-cyclohexylpropyl group, a 4-cyclohexylbutyl group, a 1-methylcyclohexyl group, a 2-methylcyclohexyl group, a 3-methylcyclohexyl group, a 4-methylcyclohexyl group, a cycloheptyl group, a norbornyl group, a norbornylmethyl group, an isobornyl group, a menthyl group, a fenchyl group, an adamantyl group, a 1-cyclopentenyl group, a 2-cyclopentenyl group, a 1-cyclohexenyl group, a 1-methyl-2-cyclohexenyl group, a 2-methyl-2,5-dicyclohexadienyl group, a phenyl group, a benzyl group, a 1-phenylcyclopropyl group, a 2-phenylcyclopropyl group, a 1-phenylcyclopentyl group, a 1-phenylethyl group, a 2-phenylethyl group, a 1-methyl-2-phenylethyl group, a 1-phenylpropyl group, a 2-phenylpropyl group, a 3-phenylpropyl group, a 4-phenylbutyl group, a 1,2,3,4-tetrahydro-2-naphthyl group, a 2-phenylethenyl group, a 3-phenyl-2-propenyl group, a 1-methyl-3-phenylethenyl group, a p-tolyl group, an m-tolyl group, an o-tolyl group, a 4-ethylphenyl group, a 4-propylphenyl group, a 4-isopropylphenyl group, a 4-butylphenyl group, a 4-t-butylphenyl group, a 1-naphthyl group and a 2-naphthyl group.

The diacyloxylation reaction step comprises stirring the 4-halo-2-halomethyl-1-butene compound (6) together with salts of carboxylic acids having corresponding $R^1$ and $R^3$, respectively, as shown in $R^1COOH$ and $R^3COOH$. When $R^1$ and $R^3$ are the same, a single type of carboxylic acid can be used.

Examples of the carboxylate salt in the diacyloxylation reaction include various metal salts and onium salts, and preferably include lithium salts, sodium salts, potassium salts, magnesium salts, calcium salts, ammonium salts, tetraalkylammonium salts and tetraalkylphosphonium salts.

The amount of the carboxylate salt may be freely selected in consideration of various conditions and is preferably 0.4 to 200 mol, more preferably 2 to 40 mol, still more preferably 2 to 20 mol relative to 1 mol of the 4-halo-2-halomethyl-1-butene compound (6) because two sites are reacted in the diacyloxylation reaction. The carboxylate salt is preferably used in an amount of 2 mol or more from the viewpoint of yield.

Examples of the solvent to be used for the diacyloxylation reaction preferably include carboxylic acids such as formic acid, acetic acid, propionic acid, and carboxylic acids having corresponding $R^1$ and $R^3$, respectively, as shown in $R^1COOH$ and $R^3COOH$; carboxylic anhydrides such as acetic anhydride, propionic anhydride, and carboxylic anhydrides having corresponding R as shown in RCO—O—COR; esters such as methyl formate, ethyl formate, methyl acetate, ethyl acetate, and methyl esters, ethyl esters, n-propyl esters and n-butyl esters of carboxylic acids having corresponding R; ethers such as diethyl ether, di-n-butyl ether, t-butyl methyl ether, cyclopentyl methyl ether, tetrahydrofuran, and 1,4-dioxane; hydrocarbons such as hexane, heptane, benzene, toluene, xylene, and cumene; chlorinated solvents such as dichloromethane, chloroform, tetrachloromethane, 1,2-dichloroethane, and 1,1,2-trichloroethane; and aprotic polar solvents such as N,N-dimethylformamide (DMF), N,N-dimethylacetamide (DMAC), N,N-dimethylpropionamide, 1,3-dimethyl-2-imidazolidinone (DMI), dimethyl sulfoxide (DMSO), and hexamethylphosphoric triamide (HMPA). The solvent is used singly or in combination of two or more. The amount of the solvent is preferably 0.1 parts to 1,000,000 parts, more preferably 1 part to 100,000 parts, still more preferably 10 parts to 10,000 parts relative to 100 parts of the 4-halo-2-halomethyl-1-butene compound (6).

When 4-halo-2-halomethyl-1-butene compound (6) is prepared from a 1-(2-chloroethyl)cyclopropyl sulfonate compound or a 1-(2-bromoethyl)cyclopropyl sulfonate compound as the 1-(2-haloethyl)cyclopropyl sulfonate compound (1), the diacyloxylation reaction may be carried by adding an iodide salt such as lithium iodide, sodium iodide, potassium iodide, magnesium iodide, calcium iodide, ammonium iodide, tetraalkylammonium iodide and tetraalkylphosphonium iodide to the reaction system, preferably in an amount of 0.0001 to 5 mol relative to 1 mol of the 1-(2-haloethyl)cyclopropyl sulfonate compound (1), while generating a 1-(2-iodoethyl)cyclopropyl sulfonate compound in situ. Alternatively, the 1-(2-iodoethyl)cyclopropyl sulfonate compound can be prepared in advance and then can undergo the reaction.

In the diacyloxylation reaction, a silver salt such as silver nitrate may also be added preferably in an amount of 0.0001 to 5 mol relative to 1 mol of the 1-(2-haloethyl)cyclopropyl sulfonate compound (1) and the resulting halide ion can be crystallized and precipitated as a silver salt (silver halide) to accelerate the reaction.

The reaction temperature during the diacyloxylation reaction is preferably 0° C. to the boiling point temperature of a solvent, more preferably 20 to 100° C. The reaction time may be freely selected and is preferably optimized by tracking the progress of the reaction by gas chromatography (GC) or thin-layer chromatography (TLC). Typically, the reaction time is preferably 5 minutes to 240 hours.

As a side reaction of the nucleophilic substitution diacyloxylation reaction, an elimination reaction of a hydrogen halide may occur competitively to form a 2-halomethyl-1,3-butadiene or a 2-acyloxymethyl-1,3-butadiene as a by-product. Although the portion of this elimination reaction is commonly small, various reaction conditions are preferably selected so as to decrease the portion of the elimination reaction and to increase the portion of the intended substitution reaction (ester formation reaction).

When the target 3-acyloxymethyl-3-butenyl carboxylate compound (3) obtained by the above diacyloxylation reaction has sufficient purity, the crude product may be subjected to the subsequent step without purification, or may be purified by a method appropriately selected from purification methods commonly used in organic synthesis, such as distillation and various types of chromatography.

By the above synthetic method of the 3-acyloxymethyl-3-butenyl carboxylate compound (3) as an electrophile, the target compound (3) is obtained in a high yield as substantially a single product in many cases. A 4-acyloxy-3-methyl-2-butenyl carboxylate or a 4-acyloxy-3-methyl-3-butenyl carboxylate as an impurity generated by positional isomerization of the double bond is hardly formed as a by-product. Due to this high selectivity, the synthetic method has advantages over conventional methods such as the method of halogenation at an allylic position of olefin by using sulfuryl chloride ($SO_2Cl_2$) reported by Veselovskii et al. (Izvestiya Akademii Nauk SSSR, Seriya Khimicheskaya, 3, 513 (1990)).

The 3-acyloxymethyl-3-butenyl carboxylate compound (3) as an electrophile synthesized as above may be subjected to a coupling reaction with a nucleophile (4) to obtain a target 4-alkyl-3-methylenebutyl carboxylate compound (5).

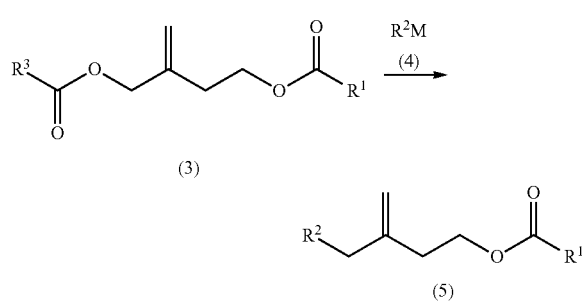

$R^2$ may be the same as or different from $R^1$ or $R^3$ and represents a chain, branched or cyclic monovalent hydrocarbon group having 1 to 10 carbon atoms and optionally containing one or more unsaturated bonds. $R^2$ may be selected to be a group corresponding to the structure of a final target compound of the synthesis. Examples of $R^2$ can include the same groups as those for $R^1$ and $R^3$.

In the present specification, as for the substituent name of $R^2$, there is no appropriate name for a monovalent substituent in which any hydrogen atom of a hydrocarbon is replaced by a bond, so that the name of an "alkyl" group corresponding to a monovalent substituent in which any hydrogen atom of the corresponding alkane is replaced by a bond is also used as the name for the monovalent substituent in which any hydrogen atom of a hydrocarbon is replaced by a bond, for convenience. Accordingly, the compound (5) is called a 4-alkyl-3-methylenebutyl carboxylate.

By appropriately selecting the conditions in the coupling reaction step, the coupling reaction at an allylic carbon having the leaving group $R^3COO$ in the compound (3) can be advanced prior to the coupling reaction at a homoallylic position having the $R^1COO$ group in the compound (3) and prior to the addition reaction to the carbonyl groups of the $R^1COO$ group and the $R^3COO$ group. Consequently, the target 4-alkyl-2-methylenebutyl carboxylate compound (5) can be obtained in a high yield.

Examples of the nucleophile (4) to be used in the coupling reaction step may include an organometallic reagent containing a group I or group II metal element or a transition metal element and having $R^2$ corresponding to the structure of a target compound.

Examples of the organometallic reagent containing a group I or group II metal element preferably include an organolithium reagent and an organomagnesium reagent (Grignard reagents) from the viewpoint of reactivity, selectivity, ease in preparation, and the like.

The organometallic reagent containing a transition metal element may be prepared by a metal exchange reaction using a stoichiometric amount (1 mol) or more of a transition metal compound with respect to 1 mol of an organolithium reagent or a Grignard reagent, or may be formed in situ from an organolithium reagent or a Grignard reagent with a transition metal compound catalyst. Examples of the transition metal compound may include transition metal compounds containing copper, iron, nickel, palladium, zinc, silver or the like, and particularly preferably include copper compounds such as copper(I) chloride, copper(I) bromide, copper(I) iodide, copper(I) cyanide, copper(I) oxide, copper(II) chloride, copper(II) bromide, copper(II) iodide, copper(II) cyanide, copper(II) oxide and dilithium tetrachlorocuprate ($Li_2CuCl_4$). The amount of the transition metal compound is from a catalytic amount (0.0001 to 0.999 mol) to a stoichiometric amount (1 mol) or an excess amount (more than 1 mol but not greater than 100 mol). A catalytic amount of the transition metal compound is particularly preferably used.

Specifically, the cationic moiety M in the nucleophile (4) is particularly preferably Li, MgQ, ZnQ, Cu, CuQ, or CuLiQ wherein Q represents a halogen atom or $R^2$.

The organometallic compound to be used as the nucleophile (4) is typically prepared from a halide having corresponding $R^2$ in a usual manner. The halide is preferably a chloride, a bromide or an iodide.

The amounts of the nucleophile (4) and the electrophile (3) to be used for the coupling reaction can be freely selected in consideration of the types of the substrates, conditions, the reaction yield, and cost efficiency such as the prices of intermediates. The nucleophile (4) is preferably used in an amount of 0.2 to 10 mol, more preferably 0.5 to 2 mol, still more preferably 0.8 to 1.5 mol relative to 1 mol of the electrophile (3). However, after the formation of the target compound, there is a possibility that the addition reaction of the nucleophile (4) to the carbonyl group of the $R^1COO$ group in the target compound (5) may further proceed. When the conditions are used in which such a side reaction proceeds, it is preferable to avoid the use of the nucleophile in an excess amount of greatly more than 1 mol relative to 1 mol of the electrophile (3).

Examples of the solvent to be used for the coupling reaction preferably include ethers such as diethyl ether, di-n-butyl ether, t-butyl methyl ether, cyclopentyl methyl ether, tetrahydrofuran and 1,4-dioxane. The solvent may be a mixed solvent of one or more ethers with one or more selected from hydrocarbons such as hexane, heptane, benzene, toluene, xylene and cumene and aprotic polar solvents such as N,N-dimethylformamide (DMF), N,N-dimethylacetamide, N,N-dimethylpropionamide, 1,3-dimethyl-2-imidazolidinone (DMI), dimethyl sulfoxide (DMSO) and hexamethylphosphoric triamide (HMPA). The amount of the solvent is not particularly limited and is preferably 0.1 part to 1,000,000 parts, more preferably 1 part to 100,000 parts, still more preferably 10 parts to 10,000 parts relative to 100 parts of the electrophile (3).

As the catalyst to be used for the coupling reaction, a lithium salt such as lithium chloride, lithium bromide and lithium iodide may be used in an amount of 0.0001 to 5 mol relative to 1 mol of the electrophile (3).

The reaction temperature for the coupling reaction is preferably −78° C. to the boiling point temperature of a solvent, more preferably −10° C. to 100° C. The reaction time may be freely selected and is preferably optimized by tracking the progress of the reaction by gas chromatography (GC) or thin-layer chromatography (TLC). Typically, the reaction time is preferably 5 minutes to 240 hours.

The target 4-alkyl-2-methylenebutyl carboxylate compound (5) obtained by the above coupling reaction may be purified by a method appropriately selected from purification methods commonly used in organic synthesis, such as distillation and various types of chromatography. Distillation is particularly preferred from the viewpoint of industrial cost efficiency.

As described above, a simple and efficient method for producing a 4-alkyl-2-methylenebutyl carboxylate compound (5) such as 7-methyl-3-methylene-7-octenyl propionate, which is the sex pheromone of SJS, is provided to supply a sufficient amount of the product for application and utilization.

EXAMPLES

The present invention will next be described in further detail with reference to Examples. It should not be construed that the present invention is limited to or by them.

As the purities of raw materials, products and intermediates, the values obtained by gas chromatographic (GC) analyses are used and expressed as % GC. GC conditions were as follows: a gas chromatograph of Shimadzu GC-14A, a column of 5% Ph-Me silicone having 0.25 mm$\phi$×25 m, a carrier gas of helium; and a flame ionization detector (FID) were used.

The crude products were optionally purified to obtain the samples for spectrum measurement.

Synthesis of 3-acyloxymethyl-3-butenyl propionate represented by General Formula (3)

Example 1

Synthesis of 3-Propionyloxymethyl-3-Butenyl Propionate which is the Compound Having $R^3=R^1=CH_3CH_2$ in General Formula (3)

As shown in the following reaction equation, 4-bromo-2-bromomethyl-1-butene is synthesized from 1-(2-bromoethyl)cyclopropyl methanesulfonate, and 3-propionyloxymethyl-3-butenyl propionate is synthesized.

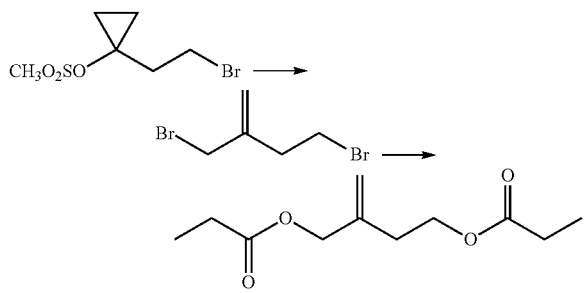

A solution of magnesium bromide in diethyl ether was prepared from 24.3 g of magnesium, 189 g of 1,2-dibromoethane and 700 ml of diethyl ether. A mixture of 122 g of 1-(2-bromoethyl)cyclopropyl methanesulfonate (75% GC) and 200 ml of toluene was added dropwise to the solution of magnesium bromide in diethyl ether, which was being stirred, heated and refluxed under a nitrogen atmosphere. The reaction mixture was refluxed for 3 hours with stirring. The reaction mixture was cooled on ice, and subjected to addition of a saturated aqueous ammonium chloride solution to separate the organic phase. The organic phase was subjected to common work-up of washing, drying and concentration to obtain 93.15 g of crude 4-bromo-2-bromomethyl-1-butene as an intermediate (75% GC, yield 81%) containing 13% GC of toluene in addition to the target compound.

Next, under a nitrogen atmosphere, a mixture of 30.0 g of the crude 4-bromo-2-bromomethyl-1-butene, 40.0 g of sodium propionate, 5.00 g of sodium iodide and 100 ml of N,N-dimethylacetamide was stirred at room temperature for 63 hours and then stirred at 70° C. for 6 hours. The reaction mixture was cooled to room temperature, subjected to addition of water, and extracted with n-hexane. The organic phase was subjected to common work-up of washing, drying and concentration to obtain 23.72 g of crude 3-propionyloxymethyl-3-butenyl propionate (72% GC). The crude product was distilled under reduced pressure to obtain 18.52 g of 3-propionyloxymethyl-3-butenyl propionate as the target compound (88% GC, yield 77%) containing 10% of 2-methylene-3-butenyl propionate generated by elimination of hydrogen bromide as a by-product in addition to the target compound.

3-Propionyloxymethyl-3-butenyl propionate

Colorless Oil
Boiling point: 78-81° C./399 Pa
IR (D-ATR): ν=2982, 2944, 1739, 1463, 1349, 1179, 1019, 910 cm$^{-1}$.
$^1$H-NMR (500 MHz, CDCl$_3$): δ=1.11 (3H, t, J=7.5 Hz), 1.14 (3H, t, J=7.5 Hz), 2.30 (2H, q, J=7.5 Hz), 2.34 (2H, q, J=7.5 Hz), 2.38 (2H, t, J=7 Hz), 4.19 (2H, t, J=7 Hz), 4.54 (2H, s), 4.99 (1H, s-like), 5.11 (1H, s) ppm.
$^{13}$C-NMR (125 MHz, CDCl$_3$): δ=9.03 (2C), 27.49, 27.51, 32.38, 62.31, 66.58, 114.73, 140.22, 173.97, 174.28 ppm.
GC-MS (EI, 70 eV): 41, 57 (base peak), 84, 111, 128, 140.

As a result of the spectral analyses of the crude 3-propionyloxymethyl-3-butenyl propionate synthesized in Example 1, 2-methylene-3-butenyl propionate as the by-product generated by the elimination of hydrogen bromide was observed, but the isomerization of the exo-methylene at the 2-position into internal olefin, for example, the formation of 2-methyl-2-butene-1,4-diyl dipropionate, was not observed. It is evident from the results that the method in accordance with the present invention achieves high selectivity.

Example 2

Synthesis of 7-Methyl-3-Methylene-7-Octenyl Propionate which is the Compound Having $R^2=CH_2=C(CH_3)-CH_2CH_2$ and $R^1=CH_3CH_2$ in General Formula (5)

As shown in the following reaction equation, 3-propionyloxymethyl-3-butenyl propionate is reacted with 3-methyl-3-butenylmagnesium bromide to obtain 7-methyl-3-methylene-7-octenyl propionate.

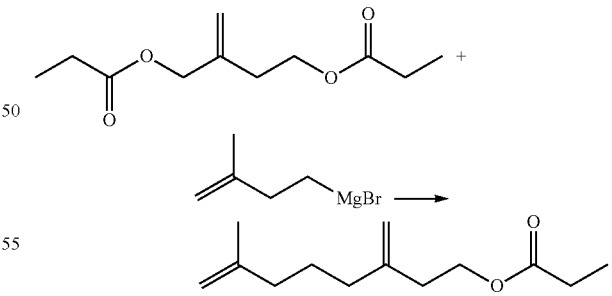

Under a nitrogen atmosphere, a mixture of 25.0 g of 3-methyl-3-butenyl bromide (83% GC), 2.50 g of 1,2-dibromoethane (used for activation of magnesium), and 200 ml of tetrahydrofuran was added dropwise to a mixture of 4.40 g of magnesium and 10 ml of tetrahydrofuran to prepare a Grignard reagent, 3-methyl-3-butenylmagnesium bromide. The Grignard reagent was added dropwise to an ice-cooled mixture of 10.0 g of crude 3-propionyloxymethyl-3-butenyl propionate (88% GC) synthesized in Example 1, 40 mg of copper(I) iodide, 60 mg of triethyl phosphite and 60 ml of tetrahydrofuran over 1 hour, while being stirred under a nitrogen atmosphere and keeping the temperature at 25° C. or less. The reaction mixture was stirred at room temperature for 17 hours. Then the reaction mixture was subjected to addition of a saturated aqueous ammonium chloride solution, and extracted with diethyl ether. The organic phase was separated and then subjected to common work-up of washing, drying and concentration to obtain 11.21 g of crude 7-methyl-3-methylene-7-octenyl propionate. The crude product was distilled under reduced pressure to obtain 7.36 g of 7-methyl-3-methylene-7-octenyl propionate (97% GC, yield 88%).

7-Methyl-3-methylene-7-octenyl propionate

Colorless Oil

IR (D-ATR): ν=3075, 2981, 2938, 1739, 1645, 1462, 1375, 1349, 1182, 1084, 889 cm$^{-1}$.

$^1$H-NMR (500 MHz, CDCl$_3$): δ=1.12 (3H, t, J=7.6 Hz), 1.53-1.61 (2H, m), 1.71 (3H, s), 1.97-2.06 (4H, m), 2.31 (2H, q, J=7.6 Hz), 2.33 (2H, t-like, J=7 Hz), 4.17 (2H, t, J=7.1 Hz), 4.67 (1H, s-like), 4.70 (1H, s-like), 4.77 (1H, s-like), 4.81 (1H, s-like) ppm.

$^{13}$C-NMR (125 MHz, CDCl$_3$): δ=9.10, 22.32, 25.51, 27.56, 34.95, 35.86, 37.29, 62.73, 109.96, 111.18, 145.44, 145.60, 174.41 ppm.

GC-MS (EI, 70 eV): 29, 41, 57 (base peak), 68, 79, 93, 107, 121, 136, 210 (M$^+$).

Having thus described certain embodiments of the present invention, it is to be understood that the invention defined by the appended claims is not to be limited by particular details set forth in the above description as many apparent variations thereof are possible without departing from the spirit or scope thereof as hereinafter claimed.

The invention claimed is:

1. A method for producing a 4-alkyl-3-methylenebutyl carboxylate compound, the method comprising:

a diacyloxylation step of subjecting a 4-halo-2-halomethyl-1-butene compound of General Formula (6):

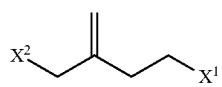

(6)

wherein X$^1$ and X$^2$ may be the same or different and each is a halogen atom,
to diacyloxylation to obtain a 3-acyloxymethyl-3-butenyl carboxylate compound of General Formula (3):

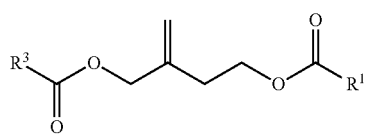

(3)

wherein R$^1$ and R$^3$ may be the same or different and each is a monovalent hydrocarbon group having 1 to 10 carbon atoms and optionally containing one or more unsaturated bonds, and a coupling step of subjecting the 3-acyloxymethyl-3-butenyl carboxylate compound (3) to a coupling reaction with an organometallic reagent of General Formula (4):

(4)

wherein R$^2$ may be the same as or different from R$^1$ or R$^3$ and is a monovalent hydrocarbon group having 1 to 10 carbon atoms and optionally containing one or more unsaturated bonds and M is Li, MgQ, ZnQ, Cu, CuQ, or CuLiQ wherein Q is a halogen atom or R$^2$, to obtain the 4-alkyl-3-methylenebutyl carboxylate compound of Formula (5):

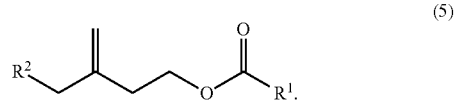

(5)

2. The method for producing a 4-alkyl-3-methylenebutyl carboxylate compound according to claim 1, wherein each of R$^1$ and R$^3$ is an ethyl group, R$^2$ is a 3-methyl-3-butenyl group and the 4-alkyl-3-methylenebutyl carboxylate compound is 7-methyl-3-methylene-7-octenyl propionate of Formula (5a):

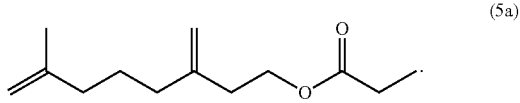

(5a)

3. The method of claim 1, wherein the halogen atom is selected from the group consisting of a chlorine atom, a bromine atom, and an iodine atom.

4. The method of claim 1, wherein at least one halogen atom is a chlorine atom.

5. The method of claim 1, wherein at least one halogen atom is a bromine atom.

6. The method of claim 1, wherein at least one halogen atom is an iodine atom.

* * * * *